United States Patent [19]
Blom et al.

[11] Patent Number: 5,741,705
[45] Date of Patent: Apr. 21, 1998

[54] METHOD FOR IN VITRO CELL GROWTH OF EUCARYOTIC CELLS USING LOW MOLECULAR WEIGHT PEPTIDES

[75] Inventors: Wim R. Blom, Houten; Anthonie Kunst; Bart J. van Schie, both of Huizen, all of Netherlands; Gregory W. Luli, Sarasota, Fla.

[73] Assignee: Quest International Flavors & Food Ingredients Company, division of Indopco, Inc., Bridgewater, N.J.

[21] Appl. No.: 393,338

[22] Filed: Feb. 23, 1995

[51] Int. Cl.$^6$ ..................................................... C12N 5/00
[52] U.S. Cl. ........................... 435/348; 435/325; 435/366; 435/404
[58] Field of Search ..................... 435/240.3, 240.31, 435/252, 325, 348, 366, 404, 240.2

[56] References Cited

U.S. PATENT DOCUMENTS

| | | | |
|---|---|---|---|
| 3,579,423 | 5/1971 | Yamane et al. | 195/1.7 |
| 3,852,479 | 12/1974 | Yokotsuka et al. | 426/44 |
| 3,932,671 | 1/1976 | Yokotsuka et al. | 426/7 |
| 4,058,512 | 11/1977 | Sievertsson et al. | 530/227 |
| 4,100,151 | 7/1978 | Alder-Nissen | 206/112 G |
| 4,235,772 | 11/1980 | Lundin et al. | 260/112.5 R |

FOREIGN PATENT DOCUMENTS

| | | |
|---|---|---|
| 0 220 379 A | 3/1987 | European Pat. Off. |
| 0249579 | 2/1990 | Japan. |
| 0418769 | 7/1992 | Japan. |
| 05236909 | 9/1993 | Japan. |

OTHER PUBLICATIONS

Nedelkovits, J. et al., Food Investigation Gazette, v. 16(4–5) pp. 211–216, plus eng. transl. 1970.

Ishii, K. et al., J. of Household Soc. of Japan, v. 45(9), pp. 791–796, plus eng. tranl., 1994.

Belitz, H.P. et al, p. 285–297, plus eng. transl., source unknown, 1982.

Babcock et al. "J. of Nutrition", v. 93, #3, Nov. 1967 pp. 368–376.

Yoong et al "Food Chem." v. 51 #2, 1994, pp. 271–274.

Heeneman et al, J. Immunological Methods, 116, 85–91 (1991).

Animal Cell Culture, A Practical Approach, Second Edition, ISBN 0–19–963213–8.

MacRitchie, J. Food Technol. 14, 595, 601 (1979).

Brand, K., et al., Metabolism 38:29–33 (1989).

Tenabe et al., Journal of Food Biochemistry, 16:235–248 (1993).

*Primary Examiner*—David M. Naff
*Assistant Examiner*—Deborah Ware
*Attorney, Agent, or Firm*—Ian C. McLeod

[57] ABSTRACT

A method and kit for growing eucaryotic cells using a hydrolyzate of a protein material containing peptides and free amino acids. The material contains L-glutamine, preferably in an amount of greater than 20 percent by weight. Ninety percent by weight of the mixture is less than 1,000 kD in molecular weight. The free amino acid level is less than 20 percent by weight and the average peptide length is less than 20 amino acids.

19 Claims, No Drawings

METHOD FOR IN VITRO CELL GROWTH OF EUCARYOTIC CELLS USING LOW MOLECULAR WEIGHT PEPTIDES

BACKGROUND OF THE INVENTION (1) Field of the Invention

The present invention relates to a novel method and kit for proliferation, propagation, maintaining and culturing of eucaryotic cells. In particular the present invention relates to the use of a protein hydrolysate, prepared using one or more hydrolytic enzymes as a basis of a medium for eucaryotic cells.

(2) Description of Related Art

Existing media for eucaryotic cells (culture media) in general comprise mixtures of amino acids, vitamins, carbohydrates and minerals. Culture media contain relatively large amounts of the amino acid L-glutamine. Typically L-glutamine is used in a cell culture medium at a concentration of about 2 mM. L-glutamine is an important energy source in proliferating eucaryotic cells and it also serves as both a carbon and a nitrogen source, especially for purine and pyrimidine synthesis.

The use of L-glutamine as an energy source in cultured mammalian cells proceeds via deamidation of L-glutamine by glutaminase to yield glutamate and ammonia. Glutamate then undergoes transamination to produce α-ketoglutaric acid which is incorporated into the energy yielding Krebbs tricarboxylic acid cycle.

The incorporation of L-glutamine in a liquid cell culture medium however suffers from the disadvantage that L-glutamine is not stable in the free amino acid form. It is well known to those skilled in the art that it rapidly decomposes into ammonia and pyroglutamic acid. Recently Heeneman et al (J. Immunological methods, 116, 85–91 (1991)) found that as a consequence of this decomposition all tested commercial media contained significantly less L-glutamine than prescribed. In addition, Heeneman et al point to the fact that the formed ammonia can be toxic to cultured cells.

When L-glutamine is incorporated in a peptide it does not decompose. It is stable provided that the L-glutamine residue is not present at the amino terminal side since at this position the L-glutamine residue can decompose into a pyroglutamic acid residue and ammonia. Peptide material containing L-glutamine residues can be obtained via the hydrolysis of suitable proteins or can be prepared synthetically.

There is abundant prior art on the hydrolysis of protein but mainly the use in food products or the use in media to grow micro-organisms is described. In general two types of protein hydrolysates can be distinguished: (1) hydrolysates comprising peptides with a chain length above about 15 amino acids and a relatively low level of free amino acids (below 10%); and (2) hydrolysates comprising peptides with a chain length below 15 amino acids and a relatively high level of free amino acids (about 15% or more).

Hydrolysates from the first group are in food applications mainly used as functional ingredients to aerate or emulsify. It is well known that for optimal functionality peptides with 15–50 amino acids residues are required. The presence of free amino acids should be avoided as these give an unwanted savory taste and smell to the product. Consequently these type of hydrolysates comprise peptides with a chain length well above 15 amino acids and a level of free amino acids below about 10%. To our knowledge hydrolysates from this group do not find an application in media to culture eucaryotic cells.

Hydrolysates from the second group are in food applications mainly used in infant and clinical formulae where a low allergenicity is required. Another preferred characteristic of these products is a reduced bitterness. In both cases the product should contain small peptides and this is achieved via the use of enzyme preparations having both endo- and exo-peptidase activity. As a consequence of the action of the exopeptidases the amount of free amino acids is strongly increased to levels of about 15% or higher.

In the fermentation industries only those hydrolysates from the second group are used which have high amounts of free amino acids (20% and preferably higher). In this case the hydrolysates are used as a relatively cheap source of free amino acids. Protein hydrolysates with a high level of free amino acids however also suffer from the disadvantage that the free glutamine decomposes into pyro-glutamic acid and the toxic ammonia and thus are not very well suited for application in cell culture media.

The prior art (e.g. Animal Cell Culture, A practical approach, second edition, ISBN 0-19-963213-8) describes the use of lactalbumin hydrolysates (prepared with pancreatin which contains both endo- and exopeptidase activity) or other peptones (hydrolysates with a very high level of free amino acids) in cell tissue culture media, but only as supplements and not as the main source of glutamine or other amino acids.

The application of synthetic peptides containing glutamine residues to our knowledge is commercially unattractive due to the very limited availability of such peptides and their relatively high price.

To our knowledge there is no description in the prior art of the use in cell culture media of larger peptides (in the form of protein hydrolysates) or intact proteins containing glutamine residues as the main or only source of glutamine and other amino acids.

OBJECTS OF THE INVENTION

It is an object of the present invention to provide a novel method and kit for the in vitro culturing of eucaryotic cells. In particular, it is an object of the present invention to provide an economic source of L-glutamine which is stable in aqueous solution, to provide an economic source of other amino acids under the conditions used to culture eucaryotic cells, which is easy to use, can be sterilized by conventional means and is free of toxic and inhibitory effects. It is further an object to provide a method and kit which is inexpensive to produce. Numerous other objects will become increasingly apparent to those skilled in the art.

DESCRIPTION OF PREFERRED EMBODIMENTS

The present invention relates to a method for maintaining or growing eucaryotic cells in vitro requiring L-glutamine by use of a culture medium, the improvement which comprises: providing a hydrolysed protein material containing peptides including L-glutamine and amino acids in a mixture in the growth medium, wherein the mixture has a free amino acid level of less than about 15 percent by total proteinaceous material weight, has an average length of the peptide which is less than about 15 amino acids and contains greater than 90 percent by total proteinaceous material weight of the peptides and amino acids with a molecular weight of less than 1000 Dalton.

Further the present invention relates to a kit for growing eucaryotic cells to be cultured which require L-glutamine for growth in vitro, the improvement which comprises: a separate container of a dry culture medium containing a hydrolysed protein material containing peptides including L-glutamine and amino acids in a mixture in the culture medium, wherein the mixture has a free amino acid level of less than about 15 percent by total proteinaceous material weight, has an average length of the peptide which is less than about 15 amino acids and contains greater than 90 percent by total proteinaceous material weight of the peptides and amino acids with a molecular weight of less than 1000 Dalton.

Preferably the mixture contains the L-glutamine in an amount of at least 20 percent by total proteinaceous material weight. Also preferably, more than about 50 percent by weight of the amount of the L-glutamine is bound to one and two amino acids. Preferably the free amino acid level is less than about 10 percent by the total proteinaceous material weight and the length of the peptide is less than 10 amino acids.

Also preferably the eucaryotic cells can be insect or mammalian cells, including human cells. Also preferably the pH is optimal for the cells. Also preferably the mixture has a pH between about 6 and 8.

In particular, the present invention relates to a method for proliferation, propagation, maintaining and culturing of eucaryotic cells in vitro by the use of a culture medium which provides a mixture of small L-glutamine residue containing peptides as the main or only source of L-glutamine and other essential amino acids, characterized in that said mixture of peptides is obtained by a controlled enzymatic hydrolysis of a protein containing raw material.

Higher eucaryotic cells in general lack the capacity of utilizing complex protein. It was thus unexpected that the hydrolyzed protein material from the present invention was able to support the culturing of eucaryotic cells. There is no clear explanation for this observation, but it may be hypothesized that eucaryotic cells apart from the sodium dependent amino acid uptake system (comprising a carrier protein) possess a mechanism via which small peptides can easily be transported into the cell.

The protein raw material of the present invention can be of animal or plant origin, examples of such proteins are milk proteins, meat proteins, soy proteins, wheat proteins, rice proteins or maize proteins. Preferably the protein raw material is wheat gluten protein or a subfraction thereof such as gliadin or glutamine.

The protein raw material is hydrolyzed by one or more hydrolytic enzymes. The hydrolytic enzyme can be of animal, plant, yeast bacterial or fungal origin. Preferably enzyme preparations are used which have a low exopeptidase activity to minimize the liberation of free amino acids. Examples of such enzyme preparations are Pepsin, Alcalase or Orientase.

The hydrolyzed protein material of the present invention is characterized by:
- a free amino acid level smaller than about 15% and
- an average peptide chain length smaller than about 15 amino acid residues.
- a molecular weight of the majority of the peptides in the hydrolysate preferably lower than 1000 Dalton.
- a level of glutamine residues in the hydrolyzed protein material preferably higher than 20%.

Published data on the composition of commonly used cell culture media reveal that these in general contain high levels of L-glutamine. To provide a protein hydrolysate also containing high levels of L-glutamine wheat gluten or subfractions thereof such as gliadine or glutenine is the preferred protein raw material. It is well known to those skilled in the art that wheat gluten contains high levels of glutamine residues (about 25–30%).

The analytical methods to determine the various relevant parameters are described below.

Analytical methods

Definitions

TN: Total Nitrogen.

AN: Alpha amino nitrogen.

EN: Epsilon amino nitrogen.

AEN: The sum of alpha and epsilon nitrogen.

PN: Nitrogen in (potential) peptide bonds (PN thus includes all AN).

FAA: Free amino acid level.

F: average amount of nitrogen per amino acid residue in a protein.

PCL: average peptide chain length.

Determination of parameters

AEN can be determined via well known methods, such as the TNBS method or via formaldehyde titration.

TN can be determined via the well known Kjeldahl method.

EN is only present in the side chain of lysine so it is equal to the amount of lysine in the product.

FAA is determined using an amino acid analyzer.

AN can be calculated from the AEN (as determined via TNBS or formaldehyde titration) and the amount of lys (=EN) in the protein hydrolysate.

$$AN=AEN-EN \tag{1}$$

PN can be approximated from TN using the average amount of nitrogen (F) per amino acid.

$$PN=TN/F \tag{2}$$

Most amino acids only have an alpha nitrogen atom but trp, lys, asn and gln have 1 extra nitrogen in the side chain, his has 2 extra nitrogen and arg has 3 extra nitrogen in the side chain.

Calculation of the average peptide chain length

The average peptide chain length can be calculated from AN and PN:

$$PCL=PN/AN \tag{3}$$

Combining eq. 2 with eq. 3 gives:

$$PCL=TN/(F*AN) \tag{4}$$

Combining eq. 4 with eq. 1 gives:

$$PCL=TN/(F*(AEN-EN)) \tag{5}$$

With eq. 5 the average peptide length in a hydrolysate is calculated in which also the FAA is taken into account. Strictly spoken an amino acid is not a peptide and FAA thus should not be included in the calculation of the average PCL. To calculate the average peptide length of the non FAA fraction, TN and AN of this fraction are required. Rewriting eq. 4 for the peptide fraction gives:

$$PCL_{pep}=TN_{pep}/(F*AN_{pep}) \tag{6}$$

in which:

$$TN_{pep} = TN - TN_{FAA} \quad (7)$$

$$TN_{FAA} = F * FAA \quad (8)$$

$$AN_{pep} = AN - FAA \quad (9)$$

Combining eq. 6 with eq. 1, 7, 8 and 9 results in:

$$PCL_{pep} = \frac{TN/F - FAA}{AEN - EN - FAA} \quad (10)$$

in which TN, AN, AEN, EN and FAA are given in mmol per weight unit.

2. Determination of molecular weight distribution

There are a number of methods to determine the molecular weight distribution. An easy and convenient method uses gel permeation chromatography. There are many, all slightly different, procedures reported in the literature.

The method referred to in this patent application uses a Protein-Pak 60 column from Waters with a length of 30 cm and an internal diameter of 7.8 mm and a Protein-Pak 125 Bulk Packing guard column. The column is eluted with a 0.1M potassium phosphate buffer with pH 7.0 at a flow rate of 1.0 ml/min. For analysis 20 μl samples containing 0.2–0.5 mg product per ml elution buffer are injected on the column. Protein and peptide peaks are detected at 214 nm.

The amount of material within a molecular weight range is determined from the area under the chromatogram in that molecular weight range.

3. Determination of glutamine levels in protein hydrolysates

Due to the instability of free L-glutamine it is not possible to determine the amount of L-glutamine in a protein based product via the normal procedure to determine the amino acid composition. In this procedure, the protein based product is treated with 6N HCl to hydrolyze it into free amino acids of which the amount can then be determined with an amino acid analyzer. During the 6N HCl hydrolysis glutamine decomposes into ammonia and pyroglutamate which is subsequently converted in glutamic acid.

An indirect method to analyze the amount of L-glutamine in a hydrolysate is to determine the amount of $NH_3$ liberated during the acid hydrolysis as described by MacRitchie (J. Food Technol. 14, 595–601 (1979)). Since $NH_3$ is not only liberated from L-glutamine but also from asparagine (which decomposes into ammonia and aspartic acid) the amount of mmol $NH_3$ liberated from a protein sample equals the amount of mmol (L-glutamine+asparagine) in the protein sample. Since the origin of the liberated $NH_3$ cannot be determined it has to be assumed that the proportion of amidated groups is the same in the two types of chains.

TABLE 1

Determination of Gln levels.

|  | Casein | Whey | Gluten |
|---|---|---|---|
| %TN | 13.7 | 14.4 | 14.0 |
| mmol $NH_3$ (=mmol Asn + Gln) | 100.0 | 73.8 | 211.8 |
| mmol Asx (analytical data) | 49.9 | 80.2 | 18.2 |
| mmol Glx (analytical data) | 140.7 | 128.1 | 239.1 |
| % (Asn + Gln)/(Asx + Glx) Analytical | 52.5 | 35.4 | 77.3 |
| % (Asn + Gln)/(Asx + Glx) Amino acid sequence | 50.1 | 38.3 |  |

We have tested the reliability of this method by determination of the amount of $NH_3$ liberated from casein and whey protein and comparing the results with the theoretical results calculated on basis of the known compositions and amino acid sequences of the individual caseins and whey proteins.

In addition the amount of $NH_3$ liberated from gluten was determined. The results are summarized in Table 2. It can be seen that there is a good agreement between the (Asn+Gln)/(Asx+Glx) ratio as determined experimentally from the analyzed amounts of liberated $NH_3$, Glx and Asx and the ratio as it should theoretically be on basis of the amino acid composition. The experimentally determined ratio for gluten (77.3%) is in line with the ratio reported by MacRitchie (75.8%).

From these results it is concluded that the determination of the amount of $NH_3$ liberated from a protein or a protein hydrolysate is a suitable method to assess the (Asn+Gln)/(Asx+Glx) ratio in a protein based product.

The following are non-limiting examples of the present invention.

EXAMPLE 1

Production of a protein hydrolysate using vital gluten

A 8% dispersion of vital gluten is hydrolyzed with 1% (E/S) of the commercially available enzyme preparation Quest neutral protease (ex Quest-Biocon, Cork, Ireland) at 50° C. for 4 hours. The pH is initially set at pH 7 and during the hydrolysis it is not controlled. After hydrolysis the enzyme is inactivated via a heat treatment of 95° C. for 1 minute. Residual intact protein and insoluble components are removed via centrifugation for 5 minutes at 2500 g and the obtained effluent is subsequently ultrafiltered. Preferably membranes with a molecular weight cutoff of 10,000 Dalton are used. The obtained ultrafiltration permeate is concentrated via evaporation and is then spray dried.

The obtained final product is characterized using the above described methods. The results are summarized in Table 2.

Evaluation of the hydrolysate in cell tissue cultures

Three media were composed on basis of the well known RPMI-1640 medium. This medium was prepared as prescribed from the RPMI-1640 select Amine kit from Gibco BRL, Life Technologies Inc., Cat. No. 17402-017 (Glascow, Scotland). The medium was divided in three equal portions which were used as basis for medium 1, 2 and 3.

To the media a supplement can be added. This supplement contains:

L-glutamine: 2 mM

Sodium pyruvate: 1 mM

Gentamycin: 55 μg/ml

β-mercapto-ethanol : 50 μM hypoxanthine: 100 μM thymidine: 15 μM fetal bovine serum: 8% (v/v)

Medium 1

To the basic RPMI-1640 medium obtained from the Gibco's select Amine kit the supplement was added.

Medium 2.

To the basic RPMI-1640 medium obtained from the Gibco's select Amine kit the supplement without the L-glutamine was added. Instead of L-glutamine as present in the supplement 2.2 g/l of the obtained gluten hydrolysate containing 3.4% free amino acids and 97.4% peptides having a molecular weight less than 1000 daltons as shown in Table 2 was added.

Additionally the free amino acids asparagine, arginine, cystine, lysine and hydroxyproline are supplemented to compensate for the low levels of these amino acids in the obtained gluten hydrolysate. Medium 3.

To the basic RPMI-1640 medium obtained from the Gibco's select Amine kit the supplement without the L-glutamine was added. Instead thereof 2.2 g/l of a mixture of free amino acids with the same composition as the obtained gluten hydrolysate was added.

Additionally the free amino acids asparagine, arginine, cystine, lysine and hydroxyproline are supplemented to compensate for the low levels of these amino acids in the obtained gluten hydrolysate.

TABLE 2

Composition of the product obtained in Example 1

| | |
|---|---|
| % AN | 1.57 |
| % TN | 14.80 |
| % FAA | 3.54 |
| PCL | 9.3 |
| >10 kD | 0.1% |
| 5–10 kD | 0.1% |
| 1–5 kD | 2.4% |
| <1 kD | 97.4% |

| | Total Amino Acids - mg/g | Free Amino Acids mg/g |
|---|---|---|
| Alanine | 23.4 | 1.9 |
| Arginine | 27.0 | 3.7 |
| Asparagine + Aspartic acid | 24.5 | 0.8 |
| Cysteine | 9.0 | 2.1 |
| Glutamine + Glutamine acid | 279.7 | 3.2 |
| Glycine | 29.9 | 0.3 |
| Histidine | 17.9 | 1.0 |
| Isoleucine | 24.7 | 1.9 |
| Leucine | 61.3 | 6.1 |
| Lysine | 12.1 | 2.0 |
| Methionine | 12.1 | 1.1 |
| Phenylalanine | 43.4 | 3.1 |
| Proline | 124.8 | 2.1 |
| Serine | 50.6 | 1.2 |
| Threonine | 24.0 | 0.8 |
| Tyrosine | 28.5 | 0.4 |
| Valine | 28.4 | 3.7 |

TABLE 3

Growth of three different cell lines on the formulated media. (Counts expressed as cell per ml).

| Cell line | Medium | day 0 | after 1 day | after 5 days | after 7 days |
|---|---|---|---|---|---|
| U266 | medium 1 | $1.7 * 10^5$ | $1.5 * 10^5$ | $1.6 * 10^5$ | $2.6 * 10^5$ |
| U266 | medium 2 | $1.2 * 10^5$ | $1.2 * 10^5$ | $1.9 * 10^5$ | $2.0 * 10^5$ |
| U266 | medium 3 | $1.1 * 10^5$ | $1.3 * 10^5$ | $1.4 * 10^5$ | $3.1 * 10^5$ |
| SP2/0 | medium 1 | $1.6 * 10^5$ | $1.4 * 10^5$ | $12.1 * 10^5$ | $16.7 * 10^5$ |
| SP2/0 | medium 2 | $0.7 * 10^5$ | $1.5 * 10^5$ | $12.5 * 10^5$ | $20.0 * 10^5$ |
| SP2/0 | medium 3 | $0.8 * 10^5$ | $0.9 * 10^5$ | $14.5 * 10^5$ | $19.8 * 10^5$ |
| Anti CD20 | medium 1 | $0.8 * 10^5$ | $1.3 * 10^5$ | $12.9 * 10^5$ | $1.5 * 10^9$ |
| Anti CD20 | medium 2 | $1.0 * 10^5$ | $1.2 * 10^5$ | $11.7 * 10^5$ | $16.5 * 10^5$ |
| Anti CD20 | medium 3 | $0.9 * 10^5$ | $1.7 * 10^5$ | $11.7 * 10^5$ | $13.5 * 10^5$ |

EXAMPLE 2

Production of a protein hydrolysate using vital gluten

A 8% dispersion of vital gluten is hydrolysed with 0.1% (E/S) of the commercially available enzyme preparation pepsin orthana 1:10,000 NF (P.C.A. Diagnostica, Haarlem, The Netherlands) at 50° C. for 16 hours. The pH is initially set at pH 1.5 with hydrochloric acid and not controlled during further hydrolysis. After hydrolysis the enzyme is inactivated via a heat treatment of 95° C. for 1 minute. Residual intact protein and insoluble components are removed via centrifugation for 5 minutes at 2500 g and the obtained effluent is subsequently ultrafiltered. Preferably membranes with a molecular weight cutoff of 10,000 Dalton are used. The obtained ultrafiltration permeate is concentrated via evaporation and is then spray dried.

The obtained final product is characterized using the above described methods. The results are summarized in Table 4.

TABLE 4

| | |
|---|---|
| % AN | 0.90 |
| % TN | 12.30 |
| % FAA | 0.70 |
| PCL | 11.9 |
| >10 kD | 1.1 |
| 5–10 kD | 1.0 |
| 1–5 kD | 7.4 |
| <1 kD | 90.5 |

| | Total Amino Acids - mg/g | Free Amino Acids mg/g |
|---|---|---|
| Alanine | 25.4 | 0.7 |
| Arginine | 24.8 | 0.0 |
| Asparagine + Aspartic acid | 33.9 | 0.8 |
| Cysteine | 4.4 | 2.1 |
| Glutamine + Glutamine acid | 162.9 | 0.0 |
| Glycine | 21.3 | 0.1 |
| Histidine | 13.5 | 0.0 |
| Isoleucine | 25.6 | 0.0 |
| Leucine | 60.8 | 0.5 |
| Lysine | 15.2 | 0.1 |
| Methionine | 13.3 | 0.1 |
| Phenylalanine | 32.7 | 0.7 |
| Proline | 55.0 | 1.1 |
| Serine | 39.2 | 0.2 |
| Threonine | 23.0 | 0.1 |
| Tyrosine | 24.3 | 0.4 |
| Valine | 28.6 | 0.1 |

Evaluation of the hydrolysate in cell tissue cultures

Two media were composed on basis of the well known RPMI-1640 medium. This medium was prepared from the RPMI-1640 select Amine kit from Gibco BRL, Life Technologies Inc., Cat No. 17402-017. The medium was divided in two equal portions which were used as basis for medium 1 and 4.

Medium 1.

To the basic RPMI-1640 medium obtained from the Gibco's select Amine kit the supplement was added as in Example 1.

Medium 4

To the basic RPMI-1640 medium obtained from the Gibco's select Amine kit the supplement without the L-glutamine was added. Instead of L-glutamine as present in the supplement 3.1 g/l of the obtained gluten hydrolysate was added. Additionally the free amino acids cysteine, arginine and hydroxyproline are supplemented to compensate for the low levels of these amino acids in the obtained gluten hydrolysate. The results are summarized in Table 5.

TABLE 5

Cell Counts
Counts are given in cell per ml.

| Cell line | Medium | day 0 | after 1 day | after 5 days | after 7 days |
|---|---|---|---|---|---|
| U266 | medium 1 | $1.7 * 10^5$ | $1.5 * 10^5$ | $1.6 * 10^5$ | $2.6 * 10^5$ |
| U266 | medium 4 | $1.4 * 10^5$ | $1.1 * 10^5$ | $1.3 * 10^5$ | $1.3 * 10^5$ |
| SP2/0 | medium 1 | $1.6 * 10^5$ | $1.4 * 10^5$ | $12.1 * 10^5$ | $16.7 * 10^5$ |
| SP2/0 | medium 4 | $1.6 * 10^5$ | $1.5 * 10^5$ | $13.6 * 10^5$ | $14.9 * 10^5$ |

TABLE 5-continued

Cell Counts
Counts are given in cell per ml.

| Cell line | Medium | day 0 | after 1 day | after 5 days | after 7 days |
|---|---|---|---|---|---|
| Anti CD20 | medium 1 | $0.8 * 10^5$ | $1.3 * 10^5$ | $12.9 * 10^5$ | $1.5 * 10^5$ |
| Anti CD20 | medium 4 | $1.1 * 10^5$ | $1.2 * 10^5$ | $14.0 * 10^5$ | $11.4 * 10^5$ |

From the results it can be seen that the gluten hydrolysate from this invention does not given an acute cytotoxicity and that the cells can be cultured using the gluten hydrolysate from this invention.

It is intended that the foregoing description be only illustrative of the present invention and that the present invention be limited only by the hereinafter appended claims.

We claim:

1. In a method for maintaining or growing eucaryotic cells in vitro requiring L-glutamine by use of a culture medium wherein the method includes culturing the cells in the culture medium, the improvement which comprises: providing a hydrolyzed protein material containing peptides as a mixture in the culture medium in an effective amount which provides a main source of the L-glutamine for the cells alone and as the peptides of at least 20% by weight of the hydrolyzed protein material, wherein the hydrolyzed protein material is obtained by enzymatic hydrolysis with an enzyme and any insoluble materials are separated from a hydrolysate and then the hydrolysate is subjected to membrane filtration, wherein the hydrolyzed protein material has a free amino acid level of less than about 15 percent of a total weight of the hydrolyzed protein material, has an average length of the peptides which is less than about 15 amino acids and contains greater than 90 percent by weight of the hydrolyzed protein material of the peptides and amino acids with a molecular weight of less than 1000 Daltons, as determined by gel permeation chromatography.

2. The method of claim 1 wherein the hydrolyzed protein material has the molecular weight less than the 1000 Daltons, as a result of the membrane filtration.

3. The method of any one of claims 1 or 2 wherein more than about 50 percent by weight of the effective amount of the L-glutamine is as a peptide.

4. The method of any one of claims 1 or 2 wherein the free amino acid level is less than about 10 percent by weight of the hydrolyzed protein material and the length of the peptides is less than 10 amino acids.

5. The method of any one of claims 1 or 2 wherein the hydrolyzed protein material is selected from the group consisting of casein, gluten, subfractions of gluten, milk protein, meat protein, soy protein, rice protein, potato protein, pea protein and maize protein.

6. The method of any one of claims 1 or 2 wherein the mixture has a pH which allows the cells to be grown in the culture medium.

7. The method of claim 6 wherein the pH of the mixture is between about 6 and 8.

8. The method of any one of claims 1 or 2 wherein the cells are mammalian.

9. The method of any one of claims 1 or 2 wherein the cells are human.

10. The method of any one of claims 1 or 2 wherein the cells are insect.

11. The method of any one of claims 1 or 2 wherein the mixture contains L-glutamine alone and as a peptide in an effective amount of at least 20 percent in the hydrolyzed protein material by weight, wherein more than about 50 percent by weight of the amount of L-glutamine is as a peptide with one or two amino acids, and wherein the free amino acid level is less than about 10 percent by weight of the total hydrolyzed protein material and the length of the peptides is less than 10 amino acids.

12. The method of any one of claims 1 or 2 wherein the enzyme is a protease.

13. The method of any one of claims 1 or 2 wherein the enzyme is a protease and the protein material is a gluten.

14. The method of any one of claims 1 or 2 wherein the enzyme is a protease and the protein material is wheat gluten.

15. In a method for maintaining or growing eucaryotic cells in vitro requiring L-glutamine by use of a culture medium wherein the method includes culturing the cells in the culture medium, the improvement which comprises: adding to the culture medium in an effective amount which provides a main source of the L-glutamine for the cells alone and as peptides of at least 20% by weight of the hydrolyzed protein material a peptide mixture obtained by enzymatic hydrolysis of a protein material, which said peptide mixture has a free amino acid level of less than 15% by weight of the hydrolyzed protein material by weight of the peptide mixture, has an average chain length of the peptides of less than 15 amino acids, contains more than 90% of the total weight of the peptide mixture of peptides with a molecular weight of less than 1000 Daltons as determined by gel permeation chromatography.

16. The method according to claim 15 wherein the hydrolyzed protein material has been subjected to a membrane filtration.

17. The method according to claim 16 wherein the membrane has a molecular weight cut-off of 10,000 Daltons.

18. The method according to any one of claims 15 or 16 wherein more than 50% by weight of the effective amount of L-gutamine is as a peptide.

19. The method according to any one of claims 15 or 16 wherein to the culture medium is also added a amino acid selected from the group consisting of asparagine, arginine, cystine, lysine and hydroxyproline to compensate for a lack of these amino acids in peptide mixture for growing the cells.

* * * * *

(12) EX PARTE REEXAMINATION CERTIFICATE (8767th)
United States Patent
Blom et al.

(10) Number: US 5,741,705 C1
(45) Certificate Issued: Dec. 20, 2011

(54) METHOD FOR IN VITRO CELL GROWTH OF EUCARYOTIC CELLS USING LOW MOLECULAR WEIGHT PEPTIDES

(75) Inventors: Wim R. Blom, Houten (NL); Anthonie Kunst, Huizen (NL); Bart J. van Schie, Huizen (NL); Gregory W. Luli, Sarasota, FL (US)

(73) Assignee: Quest International Flavors & Food Ingredients Company, division of Indopco, Inc., Bridgewater, NJ (US)

Reexamination Request:
No. 90/010,527, Jun. 10, 2009

Reexamination Certificate for:
Patent No.: 5,741,705
Issued: Apr. 21, 1998
Appl. No.: 08/393,338
Filed: Feb. 23, 1995

(51) Int. Cl.
*C12N 5/00* (2006.01)

(52) U.S. Cl. ............ 435/348; 435/325; 435/366; 435/404
(58) Field of Classification Search .............. None
See application file for complete search history.

(56) References Cited

To view the complete listing of prior art documents cited during the proceeding for Reexamination Control Number 90/010,527, please refer to the USPTO's public Patent Application Information Retrieval (PAIR) system under the Display References tab.

*Primary Examiner*—Padmashri Ponnaluri

(57) ABSTRACT

A method and kit for growing eucaryotic cells using a hydrolyzate of a protein material containing peptides and free amino acids. The material contains L-glutamine, preferably in an amount of greater than 20 percent by weight. Ninety percent by weight of the mixture is less than 1,000 kD in molecular weight. The free amino acid level is less than 20 percent by weight and the average peptide length is less than 20 amino acids.

US 5,741,705 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-19 are cancelled.

New claims 20-25 are added and determined to be patentable.

20. *In a method for maintaining or growing eucaryotic cells in vitro requiring L-glutamine by use of a culture medium, the improvement which comprises:*
   *(a) providing a hydrolyzed protein material containing peptides as a mixture in the culture medium in an effective amount which provides a main source of the L-glutamine for the cells alone and which contains at least 20% L-glutamine by weight of the hydrolyzed protein material, wherein:*
      *(i) the hydrolyzed protein material is obtained by enzymatic hydrolysis of a protein raw material with an enzyme to form a hydrolysate, separation of any insoluble materials from the hydrolysate, and then membrane filtration of the hydrolysate,*
      *(ii) the hydrolyzed protein material has a free amino acid level of less than about 15 percent of a total weight of the hydrolyzed protein material,*
      *(iii) the hydrolyzed protein material has an average length of the peptides ranging from about 9 to about 12 amino acids, and*
      *(iv) the hydrolyzed protein material contains greater than 90 percent by weight of the hydrolyzed protein material of the peptides and the free amino acids with a molecular weight of less than 1000 Daltons, as determined by gel permeation chromatography; and*
   *(b) culturing the eucaryotic cells in vitro in the culture medium.*

21. *In a method for maintaining or growing eucaryotic cells in vitro requiring L-glutamine by use of a culture medium, the improvement which comprises:*
   *(a) providing a hydrolyzed protein material containing peptides as a mixture in the culture medium in an effective amount which provides a main source of the L-glutamine for the cells alone and which contains at least 20% L-glutamine by weight of the hydrolyzed protein material, wherein:*
      *(i) the hydrolyzed protein material is obtained by enzymatic hydrolysis of a protein raw material with an enzyme to form a hydrolysate, separation of any insoluble materials from the hydrolysate, and then membrane filtration of the hydrolysate,*
      *(ii) the hydrolyzed protein material has a free amino acid level of less than about 15 percent of a total weight of the hydrolyzed protein material,*
      *(iii) the hydrolyzed protein material has an average length of the peptides of about 9 amino acids, and*
      *(iv) the hydrolyzed protein material contains greater than 90 percent by weight of the hydrolyzed protein material of the peptides and the free amino acids with a molecular weight of less than 1000 Daltons, as determined by gel permeation chromatography; and*
   *(b) culturing the eucaryotic cells in vitro in the culture medium.*

22. *In a method for maintaining or growing eucaryotic cells in vitro requiring L-glutamine by use of a culture medium, the improvement which comprises:*
   *(a) providing a hydrolyzed protein material containing peptides as a mixture in the culture medium in an effective amount which provides a main source of the L-glutamine for the cells alone and which contains at least 20% L-glutamine by weight of the hydrolyzed protein material, wherein:*
      *(i) the hydrolyzed protein material is obtained by enzymatic hydrolysis of a protein raw material with an enzyme to form a hydrolysate, separation of any insoluble materials from the hydrolysate, and then membrane filtration of the hydrolysate,*
      *(ii) the hydrolyzed protein material has a free amino acid level of less than about 15 percent of a total weight of the hydrolyzed protein material,*
      *(iii) the hydrolyzed protein material has an average length of the peptides of about 12 amino acids, and*
      *(iv) the hydrolyzed protein material contains greater than 90 percent by weight of the hydrolyzed protein material of the peptides and the free amino acids with a molecular weight of less than 1000 Daltons, as determined by gel permeation chromatography; and*
   *(b) culturing the eukaryotic cells in vitro in the culture medium.*

23. *In a method for maintaining or growing eucaryotic cells in vitro requiring L-glutamine by use of a culture medium, the improvement which comprises:*
   *(a) adding to the culture medium a hydrolyzed protein material containing peptides in an effective amount which provides a main source of the L-glutamine for the cells alone and which contains at least 20% L-glutamine by weight of the hydrolyzed protein material, wherein:*
      *(i) the hydrolyzed protein material is obtained by enzymatic hydrolysis of a protein raw material with an enzyme to form a hydrolysate and separation of any insoluble materials from the hydrolysate,*
      *(ii) the hydrolyzed protein material has a free amino acid level of less than 15% by weight of the hydrolyzed protein material,*
      *(iii) the hydrolyzed protein material has an average length of the peptides ranging from about 9 to about 12 amino acids, and*
      *(iv) the hydrolyzed protein material contains more than 90% of the total weight of the hydrolyzed protein material of the peptides and the free amino acids with a molecular weight of less than 1000 Daltons as determined by gel permeation chromatography; and*
   *(b) culturing the eucaryotic cells in the culture medium.*

24. *In a method for maintaining or growing eucaryotic cells in vitro requiring L-glutamine by use of a culture medium, the improvement which comprises:*
   *(a) adding to the culture medium a hydrolyzed protein material containing peptides in an effective amount which provides a main source of the L-glutamine for the* cells alone and which contains at least 20% L-glutamine by weight of the hydrolyzed protein material, wherein:
(i) the hydrolyzed protein material is obtained by enzymatic hydrolysis of a protein raw material with an enzyme to form a hydrolysate and separation of any insoluble materials from the hydrolysate,
(ii) the hydrolyzed protein material has a free amino acid level of less than about 15% by weight of the hydrolyzed protein material,
(iii) the hydrolyzed protein material has an average length of the peptides of about 9 amino acids, and
(iv) the hydrolyzed protein material contains more than 90% of the total weight of the hydrolyzed protein material of the peptides and the free amino acids with a molecular weight of less than 1000 Daltons as determined by gel permeation chromatography; and
(b) culturing the eucaryotic cells in the culture medium.

25. In a method for maintaining or growing eucaryotic cells in vitro requiring L-glutamine by use of a culture medium, the improvement which comprises:
(a) adding to the culture medium a hydrolyzed protein material containing peptides in an effective amount which provides a main source of the L-glutamine for the cells alone and which contains at least 20% L-glutamine by weight of the hydrolyzed protein material, wherein:
(i) the hydrolyzed protein material is obtained by enzymatic hydrolysis of a protein raw material with an enzyme to form a hydrolysate and separation of any insoluble materials from the hydrolysate,
(ii) the hydrolyzed protein material has a free amino acid level of less than 15% by weight of the hydrolyzed protein material,
(iii) the hydrolyzed protein material has an average length of the peptides of about 12 amino acids, and
(iv) the hydrolyzed protein material contains more than 90% of the total weight of the hydrolyzed protein material of the peptides and the free amino acids with a molecular weight of less than 1000 Daltons as determined by gel permeation chromatography; and
(b) culturing the eucaryotic cells in the culture medium.

* * * * *